(12) United States Patent
Moriya et al.

(10) Patent No.: US 6,682,912 B2
(45) Date of Patent: Jan. 27, 2004

(54) L-GLUTAMIC ACID-PRODUCING BACTERIUM AND METHOD FOR PRODUCING L-GLUTAMIC ACID

(75) Inventors: Mika Moriya, Kawasaki (JP); Hiroshi Izui, Kawasaki (JP); Eiji Ono, Kawasaki (JP); Kazuhiko Matsui, Kawasaki (JP); Hisao Ito, Kawasaki (JP); Yoshihiko Hara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 566 days.

(21) Appl. No.: 09/737,580

(22) Filed: Dec. 18, 2000

(65) Prior Publication Data

US 2002/0004231 A1 Jan. 10, 2002

Related U.S. Application Data

(62) Division of application No. 09/271,437, filed on Mar. 18, 1999, now Pat. No. 6,197,559.

(30) Foreign Application Priority Data

Mar. 18, 1998 (JP) .............................. 10-69106
Aug. 7, 1998 (JP) ............................ 10-224909

(51) Int. Cl.$^7$ ........................... C12P 13/14; C12N 1/00; C12N 1/20
(52) U.S. Cl. ...................... 435/110; 435/847; 435/852; 435/170
(58) Field of Search ................. 435/110, 170, 435/847, 852

(56) References Cited

U.S. PATENT DOCUMENTS

| | | | |
|---|---|---|---|
| 4,356,171 A | 10/1982 | Zalisz et al. | |
| 5,908,768 A | 6/1999 | Ono et al. | |
| 6,280,986 B1 | * 8/2001 | Hespell et al. | |

FOREIGN PATENT DOCUMENTS

| | | |
|---|---|---|
| EP | 0 670 370 | 9/1995 |
| JP | 7-203980 | 8/1995 |
| WO | 97 08294 | 3/1997 |

OTHER PUBLICATIONS

J.E. Brenchley, et al., *Regulation of the Synthesis of Enzymes Responsible for Glutamate Formation in Klebsiella Aerogenes*, The Journal of Biological Chemistry, vol. 248, No. 17, pp. 6122–6128, 1973.

D. Pulman et al., *Amino Acid Pools in Members of the Genus Erwinia Grown in Continuous Culture*, Journal of General Microbiology, 108, pp. 349–353, 1978.

ATCC Bacteria and Bacteriophages, 19$^{th}$ Edition, pp. 186–187, 1996.

Database Biosis Online! Biosciences Information Service, Philadelphia, PA, US; 1982 Regue M et al: "Transduction of Genetic Markers Associated with the S Plasmid of Klebsiella–Pneumoniae C–3 Using Bacterio Phages" Database Accession No. PREV 198477083003 XP002172698 *Abstract* & Genetica Iberica, vol. 34, No. 3–4, 1982, pp. 223–234, ISSN: 0016–6693.

* cited by examiner

Primary Examiner—Leon B. Lankford, Jr.
Assistant Examiner—Susan D. Coe
(74) Attorney, Agent, or Firm—Oblon, Spivak, McClelland, Maier & Neustadt, P.C.

(57) ABSTRACT

A method for producing L-glutamic acid which comprises culturing a microorganism belonging to the genus Klebsiella, Erwinia or Pantoea and having an ability to produce L-glutamic acid in a culture medium, and collecting produced L-glutamic acid from the culture medium. The microbial strain used is preferably a strain which decreases in or is deficient in an activity of an enzyme catalyzing a reaction branching from a pathway for L-glutamic acid biosynthesis and producing a compound other than L-glutamic acid, or a strain which increase in an activity of an enzyme catalyzing a reaction for L-glutamic acid biosynthesis.

13 Claims, 5 Drawing Sheets

SEQUENCE LISTING

<160> NUMBER OF SEQ ID NOS: 8

<210> SEQ ID NO 1
<211> LENGTH: 27
<212> TYPE: DNA
<213> ORGANISM: Artificial/Unknown
<220> FEATURE:
<221> NAME/KEY: misc_feature
<222> LOCATION: (19)..()
<223> OTHER INFORMATION: n is a, t, c, or g
<220> FEATURE:
<221> NAME/KEY: misc_feature
<222> LOCATION: ()..()
<223> OTHER INFORMATION: synthetic DNA

<400> SEQUENCE: 1
ccgggaattc ggtgacgtna artayca                                    27

<210> SEQ ID NO 2
<211> LENGTH: 29
<212> TYPE: DNA
<213> ORGANISM: Artificial/Unknown
<220> FEATURE:
<221> NAME/KEY: misc_feature
<222> LOCATION: ()..()
<223> OTHER INFORMATION: synthetic DNA

<400> SEQUENCE: 2
ggcgaattcg ggaacgggta sagytgytc                                  29

<210> SEQ ID NO 3
<211> LENGTH: 1679
<212> TYPE: DNA
<213> ORGANISM: Klebsiella planticola
<220> FEATURE:
<221> NAME/KEY: CDS
<222> LOCATION: (1)..(1677)

<400> SEQUENCE: 3

```
ggt gac gtg aaa tat cac atg ggc ttc tct tct gac atg gaa acc gaa      48
Gly Asp Val Lys Tyr His Met Gly Phe Ser Ser Asp Met Glu Thr Glu
 1               5                  10                  15 ggc ggc ctg gtg cac ctg gcg ctg gcg ttt aac ccg tca cac ctc gaa      96
Gly Gly Leu Val His Leu Ala Leu Ala Phe Asn Pro Ser His Leu Glu
             20                  25                  30 atc gtc agc ccg gtg gtt atc ggg tcg gtt cgc gcg cgt ctc gat cgt     144
Ile Val Ser Pro Val Val Ile Gly Ser Val Arg Ala Arg Leu Asp Arg
         35                  40                  45 ctc gac gag ccg agc agc aat aaa gtg ctg ccg att act atc cac ggc     192
Leu Asp Glu Pro Ser Ser Asn Lys Val Leu Pro Ile Thr Ile His Gly
     50                  55                  60 gac gcc gca gtg acg ggt cag ggc gtg gtt cag gaa acc ctg aac atg     240
Asp Ala Ala Val Thr Gly Gln Gly Val Val Gln Glu Thr Leu Asn Met
 65                  70                  75                  80 tcc aag gcg cgt ggc tac gaa gtg ggc gga acc gta cgt atc gtt atc     288
Ser Lys Ala Arg Gly Tyr Glu Val Gly Gly Thr Val Arg Ile Val Ile
                 85                  90                  95 aac aac cag gtg ggc ttc act acc tcg aac ccg ctg gat gcg cgc tcc     336
Asn Asn Gln Val Gly Phe Thr Thr Ser Asn Pro Leu Asp Ala Arg Ser
            100                 105                 110 acg cca tac tgc acc gat atc ggt aaa atg gtt cag gcg ccg atc ttc     384
Thr Pro Tyr Cys Thr Asp Ile Gly Lys Met Val Gln Ala Pro Ile Phe
        115                 120                 125 cac gtg aac gcg gac gat ccg gaa gcc gtt gct ttc gtt acc cgc ctg     432
His Val Asn Ala Asp Asp Pro Glu Ala Val Ala Phe Val Thr Arg Leu
    130                 135                 140 gcg ctg gat ttc cgt aat acc ttc aaa cgc gat gtc ttc atc gac ctg     480
Ala Leu Asp Phe Arg Asn Thr Phe Lys Arg Asp Val Phe Ile Asp Leu
145                 150                 155                 160 gtg tgc tac cgc cgt cac ggc cat aac gaa gcc gac gag ccg agc gca     528
Val Cys Tyr Arg Arg His Gly His Asn Glu Ala Asp Glu Pro Ser Ala
                165                 170                 175 acg cag ccg ctg atg tat cag aaa atc aaa aaa cat ccg acc ccg cgc     576
Thr Gln Pro Leu Met Tyr Gln Lys Ile Lys Lys His Pro Thr Pro Arg
            180                 185                 190 aaa atc tac gcc gac aaa ctt gag cag gac aaa gtg tcg acc ctg gaa     624
Lys Ile Tyr Ala Asp Lys Leu Glu Gln Asp Lys Val Ser Thr Leu Glu
        195                 200                 205 gat gcg acc gaa ctg gtt aac ctc tat cgt gat gcg ctg gat gcc ggc     672
Asp Ala Thr Glu Leu Val Asn Leu Tyr Arg Asp Ala Leu Asp Ala Gly
    210                 215                 220 gaa tgc gtg gtt gag gaa tgg cgt ccg atg aac ctg cac tcc ttt acc     720
Glu Cys Val Val Glu Glu Trp Arg Pro Met Asn Leu His Ser Phe Thr
225                 230                 235                 240 tgg tca ccg tac ctc aac cac gag tgg gat gag agc tac ccg agt aaa     768
Trp Ser Pro Tyr Leu Asn His Glu Trp Asp Glu Ser Tyr Pro Ser Lys
                245                 250                 255 gtc gag atg aaa cgt ctg cag gag ctg gct aaa cgc att agc act gtg     816
Val Glu Met Lys Arg Leu Gln Glu Leu Ala Lys Arg Ile Ser Thr Val
            260                 265                 270 ccg gac agc att gaa atg cag tct cgc gtg gcg aag att tat ggc gat     864
Pro Asp Ser Ile Glu Met Gln Ser Arg Val Ala Lys Ile Tyr Gly Asp
        275                 280                 285 cgc cag gcg atg gcc gcc ggc gag aag ctg ttc gac tgg ggg gcg gcg     912
Arg Gln Ala Met Ala Ala Gly Glu Lys Leu Phe Asp Trp Gly Ala Ala
    290                 295                 300 gaa aac ctg gct tac gcc acg ctg gtt gat gaa ggg att ccg att cgc     960
Glu Asn Leu Ala Tyr Ala Thr Leu Val Asp Glu Gly Ile Pro Ile Arg
```

| | | |
|---|---|---|
| Glu Asn Leu Ala Tyr Ala Thr Leu Val Asp Glu Gly Ile Pro Ile Arg<br>305                      310                    315                  320 | |

```
ctg tcc ggt gaa gac tcc ggt cgc ggt acg ttc ttc cac cgc cat tcc    1008
Leu Ser Gly Glu Asp Ser Gly Arg Gly Thr Phe Phe His Arg His Ser
                325                 330                 335 gtg att cat aac cag gtg aac ggt tcg acc tac acg ccg ctg cag cat    1056
Val Ile His Asn Gln Val Asn Gly Ser Thr Tyr Thr Pro Leu Gln His
            340                 345                 350 gtg cat aac ggc cag gag cat ttc aaa gtc tgg gac tcc gtg ctt tct    1104
Val His Asn Gly Gln Glu His Phe Lys Val Trp Asp Ser Val Leu Ser
        355                 360                 365 gaa gaa gcg gtg ctg gcg ttc gaa tac ggc tac gcc act gcg gaa ccg    1152
Glu Glu Ala Val Leu Ala Phe Glu Tyr Gly Tyr Ala Thr Ala Glu Pro
    370                 375                 380 cgc acc ctg act atc tgg gaa gcg cag ttc ggt gac ttt gct aac ggc    1200
Arg Thr Leu Thr Ile Trp Glu Ala Gln Phe Gly Asp Phe Ala Asn Gly
385                 390                 395                 400 gct caa gtg gtg atc gat cag ttc atc agc tcc ggc gag cag aag tgg    1248
Ala Gln Val Val Ile Asp Gln Phe Ile Ser Ser Gly Glu Gln Lys Trp
                405                 410                 415 ggc cgg atg tgt ggc ctg gtc atg ctg ctg ccg cac ggc tac gaa ggc    1296
Gly Arg Met Cys Gly Leu Val Met Leu Leu Pro His Gly Tyr Glu Gly
            420                 425                 430 cag ggc ccg gag cac tcc tcc gcg cgt ctg gaa cgc tat ctg cag ctg    1344
Gln Gly Pro Glu His Ser Ser Ala Arg Leu Glu Arg Tyr Leu Gln Leu
        435                 440                 445 tgt gct gaa cag aat atg cag gtt tgt gtg cca tcg act ccg gct cag    1392
Cys Ala Glu Gln Asn Met Gln Val Cys Val Pro Ser Thr Pro Ala Gln
    450                 455                 460 gtt tac cac atg ctg cgt cgt cag gcg ctg cgc ggt atg cgt cgt ccg    1440
Val Tyr His Met Leu Arg Arg Gln Ala Leu Arg Gly Met Arg Arg Pro
465                 470                 475                 480 ctg gtg gtg atg tcg ccg aaa tct ctg ctg cgc cat ccg ctg gcg gtc    1488
Leu Val Val Met Ser Pro Lys Ser Leu Leu Arg His Pro Leu Ala Val
                485                 490                 495 tcc agc ctg gac gag ctg gcg aac ggc acc ttc ctg ccg gcc atc ggt    1536
Ser Ser Leu Asp Glu Leu Ala Asn Gly Thr Phe Leu Pro Ala Ile Gly
            500                 505                 510 gaa atc gat gac ctc gac ccg aaa gcg gtg aag cgt gtt gtc ctg tgc    1584
Glu Ile Asp Asp Leu Asp Pro Lys Ala Val Lys Arg Val Val Leu Cys
        515                 520                 525 tct ggt aag gtt tat tac gat ctg ctg gaa caa cgc cgt aag aac gac    1632
Ser Gly Lys Val Tyr Tyr Asp Leu Leu Glu Gln Arg Arg Lys Asn Asp
    530                 535                 540 caa aaa gat gtc gct atc gtg cgt ata gaa caa ctg tac ccg ttc cc     1679
Gln Lys Asp Val Ala Ile Val Arg Ile Glu Gln Leu Tyr Pro Phe
545                 550                 555

<210> SEQ ID NO 4
<211> LENGTH: 559
<212> TYPE: PRT
<213> ORGANISM: Klebsiella planticola

<400> SEQUENCE: 4

Gly Asp Val Lys Tyr His Met Gly Phe Ser Ser Asp Met Glu Thr Glu
1               5                   10                  15

Gly Gly Leu Val His Leu Ala Leu Ala Phe Asn Pro Ser His Leu Glu
            20                  25                  30

Ile Val Ser Pro Val Val Ile Gly Ser Val Arg Ala Arg Leu Asp Arg
        35                  40                  45
```

-continued

```
Leu Asp Glu Pro Ser Ser Asn Lys Val Leu Pro Ile Thr Ile His Gly
    50                  55                  60

Asp Ala Val Thr Gly Gln Gly Val Gln Glu Thr Leu Asn Met
65              70                  75                  80

Ser Lys Ala Arg Gly Tyr Glu Val Gly Thr Val Arg Ile Val Ile
                85                  90                  95

Asn Asn Gln Val Gly Phe Thr Thr Ser Asn Pro Leu Asp Ala Arg Ser
                100                 105                 110

Thr Pro Tyr Cys Thr Asp Ile Gly Lys Met Val Gln Ala Pro Ile Phe
            115                 120                 125

His Val Asn Ala Asp Asp Pro Glu Ala Val Ala Phe Val Thr Arg Leu
    130                 135                 140

Ala Leu Asp Phe Arg Asn Thr Phe Lys Arg Asp Val Phe Ile Asp Leu
145                 150                 155                 160

Val Cys Tyr Arg Arg His Gly His Asn Glu Ala Asp Glu Pro Ser Ala
                165                 170                 175

Thr Gln Pro Leu Met Tyr Gln Lys Ile Lys Lys His Pro Thr Pro Arg
            180                 185                 190

Lys Ile Tyr Ala Asp Lys Leu Glu Gln Asp Lys Val Ser Thr Leu Glu
            195                 200                 205

Asp Ala Thr Glu Leu Val Asn Leu Tyr Arg Asp Ala Leu Asp Ala Gly
            210                 215                 220

Glu Cys Val Val Glu Glu Trp Arg Pro Met Asn Leu His Ser Phe Thr
225                 230                 235                 240

Trp Ser Pro Tyr Leu Asn His Glu Trp Asp Glu Ser Tyr Pro Ser Lys
                245                 250                 255

Val Glu Met Lys Arg Leu Gln Glu Leu Ala Lys Arg Ile Ser Thr Val
            260                 265                 270

Pro Asp Ser Ile Glu Met Gln Ser Arg Val Ala Lys Ile Tyr Gly Asp
            275                 280                 285

Arg Gln Ala Met Ala Ala Gly Leu Lys Leu Phe Asp Trp Gly Ala Ala
    290                 295                 300

Glu Asn Leu Ala Tyr Ala Thr Leu Val Asp Glu Gly Ile Pro Ile Arg
305                 310                 315                 320

Leu Ser Gly Glu Asp Ser Gly Arg Gly Thr Phe Phe His Arg His Ser
                325                 330                 335

Val Ile His Asn Gln Val Asn Gly Ser Thr Tyr Thr Pro Leu Gln His
            340                 345                 350

Val His Asn Gly Gln Glu His Phe Lys Val Trp Asp Ser Val Leu Ser
    355                 360                 365

Glu Glu Ala Val Leu Ala Phe Glu Tyr Gly Tyr Ala Thr Ala Glu Pro
370                 375                 380

Arg Thr Leu Thr Ile Trp Glu Ala Gln Phe Gly Asp Phe Ala Asn Gly
385                 390                 395                 400

Ala Gln Val Val Ile Asp Gln Phe Ile Ser Ser Gly Glu Gln Lys Trp
                405                 410                 415

Gly Arg Met Cys Gly Leu Val Met Leu Leu Pro His Gly Tyr Glu Gly
            420                 425                 430

Gln Gly Pro Glu His Ser Ser Ala Arg Leu Glu Arg Tyr Leu Gln Leu
            435                 440                 445

Cys Ala Glu Gln Asn Met Gln Val Cys Val Pro Ser Thr Pro Ala Gln
450                 455                 460
```

```
Val Tyr His Met Leu Arg Arg Gln Ala Leu Arg Gly Met Arg Arg Pro
465                 470                 475                 480

Leu Val Val Met Ser Pro Lys Ser Leu Leu Arg His Pro Leu Ala Val
                485                 490                 495

Ser Ser Leu Asp Glu Leu Ala Asn Gly Thr Phe Leu Pro Ala Ile Gly
            500                 505                 510

Glu Ile Asp Asp Leu Asp Pro Lys Ala Val Lys Arg Val Val Leu Cys
        515                 520                 525

Ser Gly Lys Val Tyr Tyr Asp Leu Leu Glu Gln Arg Arg Lys Asn Asp
    530                 535                 540

Gln Lys Asp Val Ala Ile Val Arg Ile Glu Gln Leu Tyr Pro Phe
545                 550                 555

<210> SEQ ID NO 5
<211> LENGTH: 30
<212> TYPE: DNA
<213> ORGANISM: Artificial/Unknown
<220> FEATURE:
<221> NAME/KEY: misc_feature
<222> LOCATION: ()..()
<223> OTHER INFORMATION: synthetic DNA

<400> SEQUENCE: 5
tactgggtca cctgacagct tatcatcgat                                      30

<210> SEQ ID NO 6
<211> LENGTH: 30
<212> TYPE: DNA
<213> ORGANISM: Artificial/Unknown
<220> FEATURE:
<221> NAME/KEY: misc_feature
<222> LOCATION: ()..()
<223> OTHER INFORMATION: synthetic DNA

<400> SEQUENCE: 6
cgttcggtga ccaccaaagc ggccatcgtg                                      30

<210> SEQ ID NO 7
<211> LENGTH: 27
<212> TYPE: DNA
<213> ORGANISM: Artificial/Unknown
<220> FEATURE:
<221> NAME/KEY: misc_feature
<222> LOCATION: ()..()
<223> OTHER INFORMATION: synthetic DNA

<400> SEQUENCE: 7
ggggtaccca aataggcgta tcacgag                                         27

<210> SEQ ID NO 8
<211> LENGTH: 26
<212> TYPE: DNA
<213> ORGANISM: Artificial/Unknown
<220> FEATURE:
<221> NAME/KEY: misc_feature
<222> LOCATION: ()..()
<223> OTHER INFORMATION: synthetic DNA

<400> SEQUENCE: 8
ggggtacccg cgatggatat gttctg                                          26
```

L-GLUTAMIC ACID-PRODUCING BACTERIUM AND METHOD FOR PRODUCING L-GLUTAMIC ACID

This application is a Divisional of U.S. application Ser. No. 09/271,437, filed on Mar. 18, 1999, now U.S. Pat. No. 6,197,559.

BACKGROUND OF THE INVENTION

The present invention relates to a novel L-glutamic acid-producing bacterium and a method for producing L-glutamic acid by fermentation using the same. L-Glutamic acid is an important amino acid as food, drugs and the like.

L-Glutamic acid has conventionally been produced by fermentation methods utilizing the so-called coryneform L-glutamic acid-producing bacteria which principally belong to the genera Brevibacterium, Corynebacterium, and Microbacterium or variants thereof ("Amino Acid Fermentation", Gakkai Shuppan Center, pp. 195–215, 1986). As methods for producing L-glutamic acid by fermentation utilizing other bacterial strains, there have been known the methods utilizing microorganisms of the genera Bacillus, Streptomyces, Penicillium and the like (U.S. Pat. No. 3,220,929), the methods utilizing microorganisms of the genera Pseudomonas, Arthrobacter, Serratia, Candida and the like (U.S. Pat. No. 3,563,857), the methods utilizing variant strains of *Escherichia coli* (Japanese Patent Application Laid-Open (KOKAI) No. 5-244970(1993)) and the like.

Though the productivity of L-glutamic acid has considerably been improved by breeding of such microorganisms as mentioned above or improvements of production methods, it is still desired to develop a more inexpensive and more efficient method for producing L-glutamic acid in order to meet the expected markedly increasing future demand of the amino acid.

SUMMARY OF THE INVENTION

The object of the present invention is to find novel L-glutamic acid-producing bacterium having a high ability to produce L-glutamic acid, thereby developing a more inexpensive and more efficient method for producing L-glutamic acid.

To achieve the aforementioned object, the present inventors intensively searched for and studied microorganisms having the ability to produce L-glutamic acid that are different from the previously reported microorganisms. As a result, they found that certain strains derived from microorganisms belonging to the genus Klebsiella or the genus Erwinia had a high ability to produce L-glutamic acid, and have completed the present invention.

Thus the present invention provides:

(1) a microorganism belonging to the genus Klebsiella, the genus Erwinia or the genus Pantoea and having an ability to produce L-glutamic acid;
(2) a microorganism of the above (1) which is *Klebsiella planticola* or *Pantoea agglomerans*;
(3) a microorganism of the above (1) or (2) which increases in an activity of an enzyme catalyzing a reaction for L-glutamic acid biosynthesis;
(4) a microorganism of the above (3) wherein the enzyme catalyzing the reaction for the L-glutamic acid biosynthesis is at least one selected from the group consisting of citrate synthase (abbreviated as "CS" hereinafter), phosphoenolpyruvate carboxylase (abbreviated as "PEPC" hereinafter), and glutamate dehydrogenase (abbreviated as "GDH" hereinafter);
(5) a microorganism of the above (4) wherein the enzyme catalyzing the reaction for the L-glutamic acid biosynthesis includes all of CS, PEPC, and GDH;
(6) a microorganism of any one of the above (1) to (5) which decreases in or is deficient in an activity of an enzyme catalyzing a reaction branching from a pathway for L-glutamic acid biosynthesis and producing a compound other than L-glutamic acid;
(7) a microorganism of the above (6) wherein the enzyme catalyzing the reaction branching from the pathway for L-glutamic acid biosynthesis and producing the compound other than L-glutamic acid is α-ketoglutarate dehydrogenase (abbreviated as "αKGDHO" hereinafter); and
(8) a method for producing L-glutamic acid which comprises culturing the microorganism as defined in any one of the above (1) to (7) in a liquid culture medium to produce and accumulate L-glutamic acid in the culture medium, and collecting the L-glutamic acid from the culture medium.

Because the microorganism of the present invention have a high ability to produce L-glutamic acid, it is considered to be possible to impart a further higher production ability to the microorganism by using the breeding techniques previously known for the coryneform L-glutamic acid-producing bacteria and the like, and it is expected to contribute to development of a more inexpensive and more efficient method for producing L-glutamic acid by appropriately selecting culture conditions and the like.

DETAILED DESCRIPTION OF THE INVENTION

Figure 1:
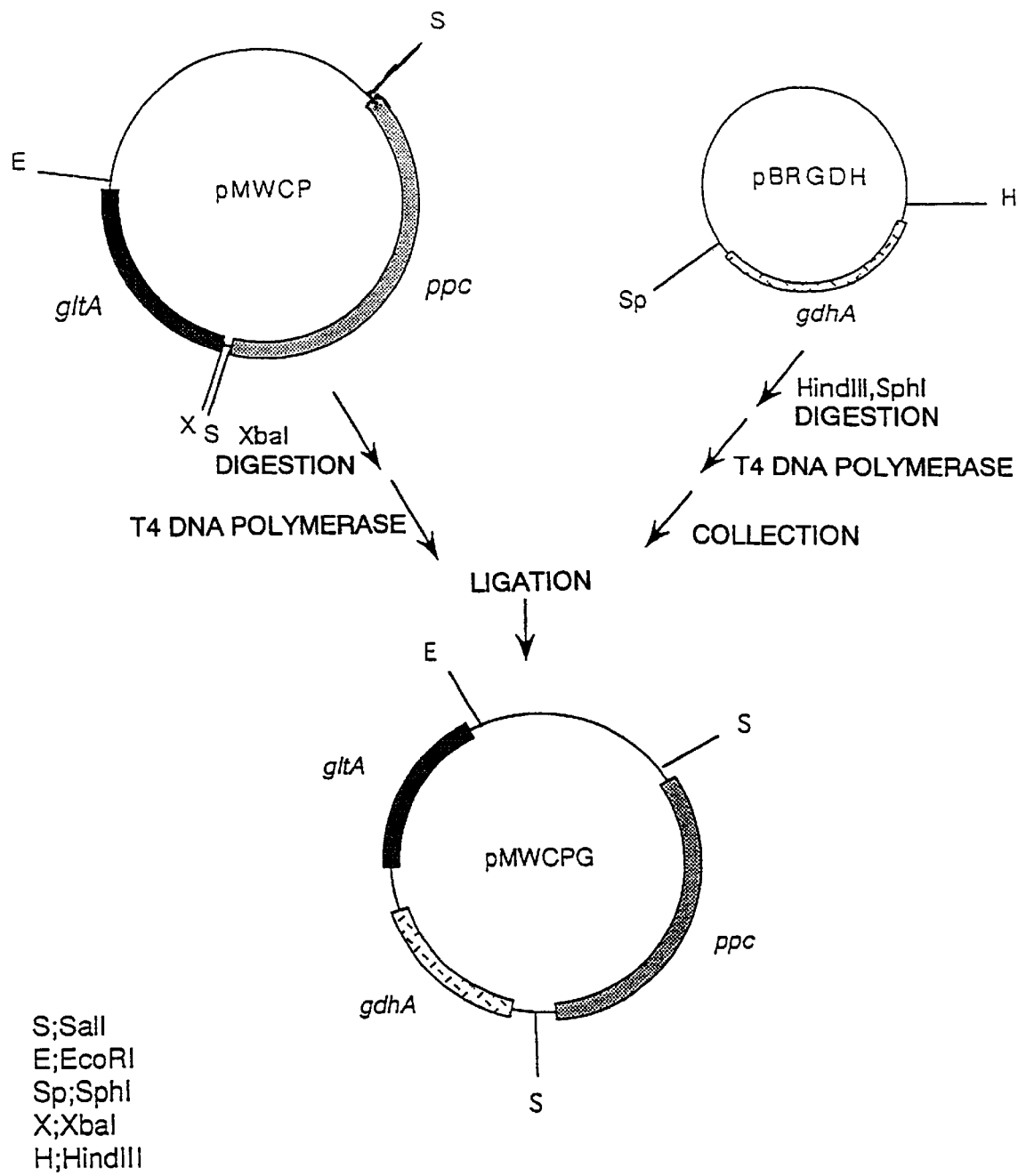
FIG. 1 shows construction of a plasmid pMWCPG having a gltA gene, a ppc gene and a gdhA gene.

The present invention will be explained in detail hereinafter.

Examples of the microorganism belonging to the genus Klebsiella, Erwinia or Pantoea that can be used for the present invention are listed below.

*Klebsiella planticola*
*Klebsiella terrigena*
*Erwinia herbicola* (now classified as *Pantoea agglomerans*)
*Erwinia ananas*
*Erwinia cacticida*
*Erwinia chrysanthemi*
*Erwinia mallotivora*
*Erwinia persicinus*
*Erwinia psidii*
*Erwinia quercina*

*Erwinia rhapontici*
*Erwinia rubrifaciens*
*Erwinia salicis*
*Erwinia uredovora*
*Pantoea agglomerans*
*Pantoea dispersa*

More preferably, those bacterial strains listed below can be mentioned:

*Klebsiella planticola* AJ13399
*Erwinia herbicola* IAM1595 (*Pantoea agglomerans* AJ2666)

The *Klebsiella planticola* AJ13399 was deposited at the National Institute of Bioscience and Human-Technology, Agency of Industrial Science and Technology, Ministry of International Trade and Industry on Feb. 19, 1998, and received an accession number of FERM P-16646, and then transferred to an international deposition under the Budapest Treaty on Jan. 11, 1999, and received an accession number of FERM BP-6616. Microorganisms which have been classified as *Erwinia helbicola* are now classified as *Pantoea agglomerans*. Therefore, the *Erwinia herbicola* IAM1595 is designated as *Pantoea agglomerans* AJ2666, and was deposited at the National Institute of Bioscience and Human-Technology, Agency of Industrial Science and Technology, Ministry of International Trade and Industry on Feb. 25, 1999 as an international deposition under the Budapest Treaty and received an accession number of FERM BP-6660.

The *Klebsiella planticola* AJ13399 is a strain isolated from soil in Sapporo-shi, Hokkaido, Japan.

Physiological properties of AJ13399 are as follows:

(1) Cell morphology: Rod-shaped
(2) Motility: Absent
(3) Spore formation: Absent
(4) Colony morphology on LabM nutrient agar: Circular, smooth surface, cream in color, even, raised, and glistening
(5) Glucose OF test: Positive for fermentability
(6) Gram stain: Negative
(7) Behavior for oxygen: Facultative anaerobe
(8) Catalase: Positive
(9) Oxidase: Negative
(10) Urease: Positive
(11) Cytochrome oxidase: Negative
(12) β-Galactosidase: Positive
(13) Arginine dehydratase: Negative
(14) Ornithine decarboxylase: Negative
(15) Lysine decarboxylase: Positive
(16) Tryptophan deaminase: Negative
(17) Voges-Proskauer reaction: Positive
(18) Indole production: Positive
(19) Hydrogen sulfide production in TSI culture medium: Negative
(20) Citric acid assimilability: Positive
(21) m-Hydroxybenzene acid assimilability: Negative
(22) Gelatin liquefaction: Negative
(23) Production of acid from sugar
  Glucose: Positive
  Mannitol: Positive
  Rhamnose: Positive
  Arabinose: Positive
  Sucrose: Positive
  Sorbitol: Positive
  Inositol: Positive
  Melibiose: Positive
  Amygdalin: Positive
  Adonitol-peptone-water: Positive
  Cellobiose-peptone-water: Positive
  Dulcitol-peptone-water: Negative
  Raffinose-peptone-water: Positive
(23) Growth temperature: Good growth at 37° C., no growth at 45° C.

From these bacteriological properties, AJ13399 is determined to be *Klebsiella planticola*.

In the "Bergey's Manual of Determinative Bacteriology, ninth edition," *Erwinia helbicola* is not described and microorganisms which have been classified as *Erwinia helbicola* are classified as *Pantoea agglomerans*. Thus the microorganisms belonging to genus Erwinia and the microorganisms belonging to the genus Pantoea are closely related to each other. Therefore, any of microorganisms belonging to the genus Erwinia and the genus Pantoea can be used in the present invention.

The sugar metabolism by bacteria belonging to the genus Klebsiella, Erwinia or Pantoea such as those mentioned above is achieved via the Embden-Meyerhof pathway, and pyruvate produced in the pathway is oxidized in the tricarboxylic acid cycle as for aerobic conditions. L-Glutamic acid is biosynthesized from α-ketoglutaric acid which is an intermediate of the tricarboxylic acid cycle by GDH or glutamine synthetase/glutamate synthase. Thus, these microorganisms share the same biosynthetic pathway for L-glutamic acid, and microorganisms belonging to the genus Klebsiella, Erwinia or Pantoea are encompassed within a single concept according to the present invention. Therefore, microorganisms belonging to the genus Klebsiella, Erwinia or Pantoea other than species and strains specifically mentioned above also fall within the scope of the present invention.

The microorganism of the present invention is a microorganism belonging to the genus Klebsiella, Erwinia or Pantoea and having an ability to produce L-glutamic acid. The expression "having an ability to produce L-glutamic acid" as herein used means to have an ability to accumulate L-glutamic acid in a culture medium during cultivation. The ability to produce L-glutamic acid may be either one possessed by a wild-type strain as its property, or one imparted or enhanced by breeding. The examples of the microorganism belonging to the genus Klebsiella, Erwinia or Pantoea and having the ability to produce L-glutamic acid include, for example, such microorganisms which increase in an activity of an enzyme catalyzing a reaction for L-glutamic acid biosynthesis, and such microorganisms which decrease in or are deficient in an activity of an enzyme catalyzing a reaction branching from a pathway for L-glutamic acid biosynthesis and producing a compound other than L-glutamic acid. The examples of the microorganism further include those increasing in the activity of the enzyme catalyzing the reaction for the L-glutamic acid biosynthesis, and decreasing in or being deficient in the activity of the enzyme catalyzing the reaction branching from the pathway for L-glutamic acid biosynthesis and producing the compound other than L-glutamic acid.

As examples of the enzyme catalyzing the reaction for L-glutamic acid biosynthesis, there can be mentioned GDH, glutamine synthetase, glutamate synthase, isocitrate dehydrogenase, aconitate hydratase, CS, PEPC, pyruvate dehydrogenase, pyruvate kinase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase and the like. Among these enzymes, one or two or three kinds of CS, PEPC and GDH are preferred. As for the microorganism of the present invention, it is further preferred that activities of all of the three kinds of enzymes, CS, PEPC and GDH, are increased. Whether a microorganism increases in an activity of a target enzyme, and degree of the increase of the activity can be determined by measuring the enzyme activity of a bacterial cell extract or a purified fraction, and comparing it with that of a wild type strain or a parent strain.

The microorganism of the present invention, which belongs to the genus Klebsiella, Erwinia or Pantoea, and increases in the activity of the enzyme catalyzing the reaction for L-glutamic acid biosynthesis, can be obtained as, for example, a variant where mutation has been made in a gene encoding the enzyme or a genetic recombinant strain by using any of the microorganisms mentioned above as a starting parent strain.

To enhance the activity of CS, PEPC or GDH, for example, a gene encoding CS, PEPC or GDH can be cloned in a suitable plasmid, and the aforementioned starting parent strain as a host can be transformed with the resulting plasmid. This can increase the copy number of each of the genes encoding CS, PEPC and GDH (hereinafter abbreviated as "gltA gene", "ppc gene", and "gdhA gene", respectively), and as a result the activities of CS, PEPC and GDH can be increased.

One or two or three kinds selected from the cloned gltA gene, ppc gene and gdha gene in any combination are introduced into the starting parent strain mentioned above. When two or three kinds of the genes are introduced, either the two or three kinds of the genes are cloned in one kind of plasmid, and introduced into the host, or they are separately cloned in two or three kinds of plasmids that can exist in the same host, and introduced into the host.

The plasmid is not particularly limited so long as it can autonomously replicate in a microorganism belonging to the genus Klebsiella, Erwinia or Pantoea. Examples of the plasmid include, for example, pUC19, pUC18, pBR322, pHSG299, pHSG298, pHSG399, pHSG398, RSF1010, pMW119, pMW118, pMW219, pMW218 and the like. Other than these plasmids, phage DNA vectors can also be utilized.

Transformation can be achieved by, for example, the method of D. M. Morrison (Methods in Enzymology 68, 326 (1979)), the method by increasing permeability of recipient cells for DNA with calcium chloride (Mandel, M. and Higa, A., J. Mol. Biol., 53, 159 (1970)), or the like.

The activities of CS, PEPC and GDH can also be increased by using multiple copies of the gltA gene, the ppc gene and/or the gdh gene present on the chromosome DNA of the starting parent strain as a host. In order to introduce multiple copies of the gltA gene, the ppc gene and/or the gdhA gene into a chromosome DNA of a microorganism belonging to the genus Klebsiella, Erwinia or Pantoea, sequences present on chromosome DNA in a multiple copy number such as repetitive DNA, and inverted repeats present at an end of transposition factors can be utilized. Alternatively, multiple copies of the genes can also be introduced into a chromosome DNA by utilizing transposition of transposons carrying the gltA gene, the ppc gene, or the gdhA gene. These techniques can increase the copy number of the gltA gene, the ppc gene, and the gdhA gene in transformant cells, and as a result increase the activities of CS, PEPC and GDH.

Any organisms can be used as a source of the gltA gene, the ppc gene and the gdha gene used for increasing the copy numbers, so long as the organisms have the CS, PEPC and GDH activities. Among such organisms, bacteria, i.e.,. prokaryotes, such as those bacteria belonging to the genus Enterobacter, Klebsiella, Erwinia, Pantoea, Serratia, Escherichia, Corynebacterium, Brevibacterium, or Bacillus are preferred. As a specific example, *Escherichia coli* can be mentioned. The gltA gene, the ppc gene and the gdhA gene can be obtained from a chromosome DNA of such microorganisms as mentioned above.

The gltA gene, the ppc gene and the gdhA gene can each be obtained from a chromosome DNA of any of the aforementioned microorganisms by isolating a DNA fragment complementing auxotrophy of a variant strain lacking the CS, PEPC or GDH activity. Alternatively, because the nucleotide sequences of these genes of bacteria of the genus Escherichia or Corynebacterium have already been elucidated (Biochemistry, Vol. 22, pp.5243–5249, 1983; J. Biochem. Vol. 95, pp.909–916, 1984; Gene, Vol. 27, pp.193–199, 1984; Microbiology, Vol. 140, pp.1817–1828, 1994; Mol. Gen. Genet. Vol. 218, pp.330–339, 1989; and Molecular Microbiology, Vol. 6, pp 317–326, 1992), the genes can be obtained by PCR using primers synthesized based on each of the elucidated nucleotide sequences, and the chromosome DNA as a template.

The activity of CS, PEPC or GDH can also be increased by, other than by the gene amplification mentioned above, enhancing expression of the gltA gene, the ppc gene or the gdhA gene. For example, the expression is enhanced by replacing the promoter of the gltA gene, the ppc gene, or the gdhA gene with another stronger promoter. Examples of such a strong promoter include, for example, a lac promoter, a trp promoter, a trc promoter, a tac promoter, a $P_R$ promoter and a $P_L$ promoter of lambda phage and the like. The gltA gene, the ppc gene, or the gdhA gene of which promoter has been substituted is cloned into a plasmid and introduced into a host microorganism, or introduced into a chromosome DNA of host microorganism using a repetitive DNA, inverted repeat, transposon or the like.

The activities of CS, PEPC or GDH can also be increased by replacing the promoter of the gltA gene, the ppc gene, or the gdha gene on a chromosome with another stronger promoter (see WO87/03006, and Japanese Patent Application Laid-Open (KOKAI) No. 61-268183(1986)), or inserting a strong promoter at the upstream of each coding sequence of the genes (see Gene, 29, pp.231–241, 1984). Specifically, these are achieved by homologous recombination between the gltA gene, the ppc gene, or the gdha gene of which promoter is replaced with a stronger promoter or DNA containing a part of them, and a corresponding gene on the chromosome.

Specific examples of the microorganism belonging to the genus Klebsiella, Erwinia or Pantoea of which CS, PEPC or GDH activity is increased include, for example, *Klebsiella planticola* ATJ13399/RSFCPG, and *Erwinia herbicola* IAM1595/RSFCPG.

Examples of the enzyme catalyzing the reaction branching from the pathway of L-glutamic acid biosynthesis and producing the compound other than L-glutamic acid include, for example, αKGDH, isocitrate lyase, phosphate acetyltransferase, acetate kinase, acetohydroxy acid synthase, acetolactate synthase, formate acetyltransferase, lactate dehydrogenase, L-glutamate decarboxylase, 1-pyrroline dehydrogenase and the like. Among these enzymes, αKGDH is preferred.

In order to obtain such decrease or deficiency of enzyme activity as mentioned above in a microorganism belonging to the genus Klebsiella, Erwinia or Pantoea, a mutation causing the decrease or deficiency of the enzyme activity can be introduced into a gene encoding the enzyme by a conventional mutagenesis technique or genetic engineering technique.

Examples of the mutagenesis technique include, for example, the method utilizing irradiation of X-ray or ultraviolet light, the method utilizing treatment with a mutagenic agent such as N-methyl-N'-nitro-N-nitrosoguanidine and the like. The site of gene to which a mutation is introduced may be a coding region encoding an enzyme protein, or an expression regulatory region such as a promoter.

Examples of the genetic engineering technique include, for example, genetic recombination, genetic transduction, cell fusion and the like. For example, a drug resistance gene is inserted into a target gene to produce a functionally inactivated gene (defective gene). Then, this defective gene is introduced into a cell of a microorganism belonging to the genus Klebsiella, Erwinia or Pantoea, and the target gene on a chromosome is replaced with the defective gene by homologous recombination (gene disruption).

Whether a microorganism decreases in an activity of a target enzyme or is deficient in the activity, or degree of the decrease of the activity can be determined by measuring the enzyme activity of a bacterial cell extract or a purified fraction of a candidate strain, and comparing it with that of a wild-type strain or a parent strain. The αKGDH enzymatic activity can be measured by, for example, the method of Reed et al. (L. J. Reed and B. B. Mukherjee, Methods in Enzymology 1969, 13, p.55–61).

Depending on the target enzyme, a target variant can be selected based on a phenotype of the variant. For example, a variant which is deficient in the αKGDH activity or decreases in the activity cannot grow on a minimal medium containing glucose, or a minimal medium containing acetic acid or L-glutamic acid as an exclusive carbon source, or shows markedly reduced growth rate therein under aerobic conditions. However, even under the same condition, it can exhibit normal growth by addition of succinic acid or lysine, methionine and diaminopimelate to the minimal medium containing glucose. Based on these phenomena, a variant that is deficient in the αKGDH activity or decreases in the activity can be selected.

A method for producing a *Brevibacterium lactofermentum* strain lacking the αKGDH gene based on homogenous recombination is detailed in WO95/34672, and a similar method can be used for microorganisms belonging to the genus Klebsiella, Erwinia or Pantoea.

In addition, procedures of genetic cloning, cleavage and ligation of DNA, transformation and the like are detailed in Molecular Cloning, 2nd edition, Cold Spring Harbor Press (1989) and the like.

An example of the variant strain that is deficient in the αKGDH activity or decreases in the activity obtained as described above is *Klebsiella planticola* AJ13410. The *Klebsiella planticola* AJ13410 was deposited at the National Institute of Bioscience and Human-Technology, Agency of Industrial Science and Technology, Ministry of International Trade and Industry on Feb. 19, 1998, received an accession number of FERM P-16647, and then transferred to an international deposition under the Budapest Treaty on Jan. 11, 1999, and received an accession number of FERM BP-6617.

Bacterial strains belonging to the gunus Klebsiella, Erwinia or Pantoea and decreasing in the activity of αKGDH activity or being deficient in the activity, or those increasing in the activity of CS, PEPC or GDH obtained as described above would have the ability to produce L-glutamic acid as shown in the examples hereinafter.

As for microorganisms belonging to the genus Escherichia, which is classified into the enteric bacteria like the genus Klebsiella, Erwinia or Pantoea, there have been known that strains which decrease in the activity of the αKGDH or are deficient in the activity may produce L-glutamic acid (Japanese Patent Application Laid-Open No. 5-244970(1993)), that strains which decrease in the activity of the αKGDH or are deficient in the activity and increase in the activities of PEPC and GDH may produce a further increased amount of L-glutamic acid (Japanese Patent Application Laid-Open No. 7-203980(1995)), and that strains exhibiting valine sensitivity and having enhanced activities of CS and GDH may produce L-glutamic acid (WO97/08294).

As for microorganisms belonging to the genus Enterobacter, which is similarly classified into the enteric bacteria, the present inventors found that strains which decrease in the activity of the αKGDH or are deficient in the activity, or strains which increase in activities of PEPC, GDH and CS may produce L-glutamic acid (Japanese Patent Application No. 10-69068(1998)).

Further, as also for microorganisms belonging to the genus Serratia, the present inventors found that strains having enhanced activities of PEPC, GDH and CS may produce L-glutamic acid (Japanese Patent Application No. 10-69068(1998)).

From these facts, it is readily expected, as for bacteria belonging to the genus Klebsiella, Erwinia, Pantoea, Escherichia, Enterobactar or Serratia other than the strains described in the Examples, that strains decreasing in the activity of the αKGDH or being deficient in the activity, or strains increasing in the activities of PEPC, GDH and CS may produce L-glutamic acid. As demonstrated in the Examples, it is strongly supported that the fact that the ability to produce L-glutamic acid could be imparted to *Klebsiella planticola* AJ13399 by deleting the αKGDH may be applied to the other bacteria of the genus Klebsiella, Erwinia or Pantoea.

L-Glutamic acid can be produced by culturing the microorganism belonging to the genus Klebsiella, Erwinia or Pantoea and having the ability to produce L-glutamic acid in a liquid culture medium to produce and accumulate L-glutamic acid in the medium, and collecting it from the culture medium.

The culture medium may be an ordinary nutrient medium containing a carbon source, a nitrogen source, and inorganic salts, as well as organic nutrients such as amino acids, vitamins and the like, as required. It can be a synthetic medium or a natural medium. Any carbon sources and nitrogen sources can be used for the culture medium so long as they can be utilized by the microorganism to be cultured.

The carbon source may be a saccharide such as glucose, glycerol, fructose, sucrose, maltose, mannose, galactose, starch hydrolysates, molasses and the like. Further, an organic acid such as acetic acid and citric acid may also be used alone or in combination with other carbon sources.

The nitrogen source may be ammonia, ammonium salts such as ammonium sulfate, ammonium carbonate, ammonium chloride, ammonium phosphate, and ammonium acetate, nitrates and the like.

As organic trace nutrients, amino acids, vitamins, fatty acids, nucleic acids, materials containing them such as peptone, casamino acid, yeast extract, and soybean protein decomposition products and the like are used, and when an auxotrophic variant which requires an amino acid or the like for its growth is used, it is necessary to complement the nutrient required.

As the inorganic salt, phosphates, magnesium salts, calcium salts, iron salts, manganese salts and the like are used.

As for the culture conditions, cultivation may be performed under aerobic conditions at a temperature of 20 to 42° C. and a pH of 4 to 8. The cultivation can be continued for 10 hours to 4 days to accumulate a considerable amount of L-glutamic acid in the liquid culture medium.

After the completion of the cultivation, L-glutamic acid accumulated in the culture medium may be collected by a known method. For example, it can be isolated by a method comprising concentrating the medium after removing the cells to crystallize the product, ion exchange chromatography or the like.

EXAMPLES

The present invention will be explained more specifically with reference to the following examples.

(1) Construction of Plasmid having gltA Gene, ppc Gene and gdhA Gene

Procedure for construction of a plasmid having a gltA gene, a ppc gene and a gdhA gene will be explained by referring to FIGS. 1, 2 and 3.

A plasmid pBRGDH having a gdha gene derived from *Escherichia coli* (Japanese Patent Application Laid-Open (KOKAI) No. 7-203980(1995)) was digested with HindIII and SphI, and the both ends were blunt-ended by a treatment with T4 DNA polymerase. Then, a DNA fragment containing the gdha gene was purified and collected. On the other hand, a plasmid pMWCP having a gltA gene and a ppc gene derived from *Escherichia coli* (WO97/08294) was digested with XbaI, and the both ends were blunt-ended by a treatment with T4 DNA polymerase. This was mixed with the DNA fragment having the gdhA gene purified above, and ligated with T4 ligase, giving a plasmid pMWCPG, which corresponds to the pMWCP further carrying the gdhA gene (FIG. 1).

Figure 2:
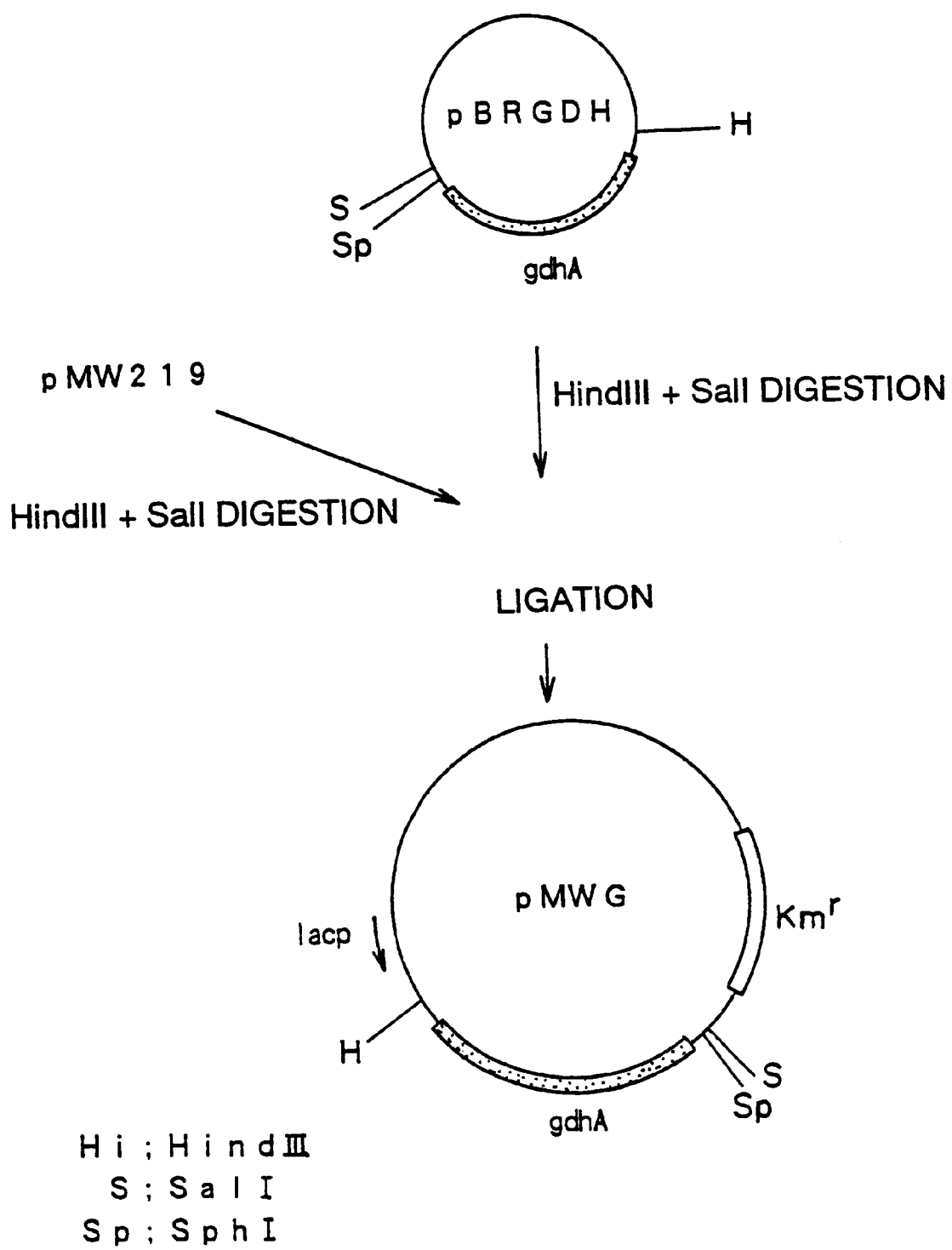
FIG. 2 shows construction of a plasmid pMWG having the gdhA gene.
Figure 3:
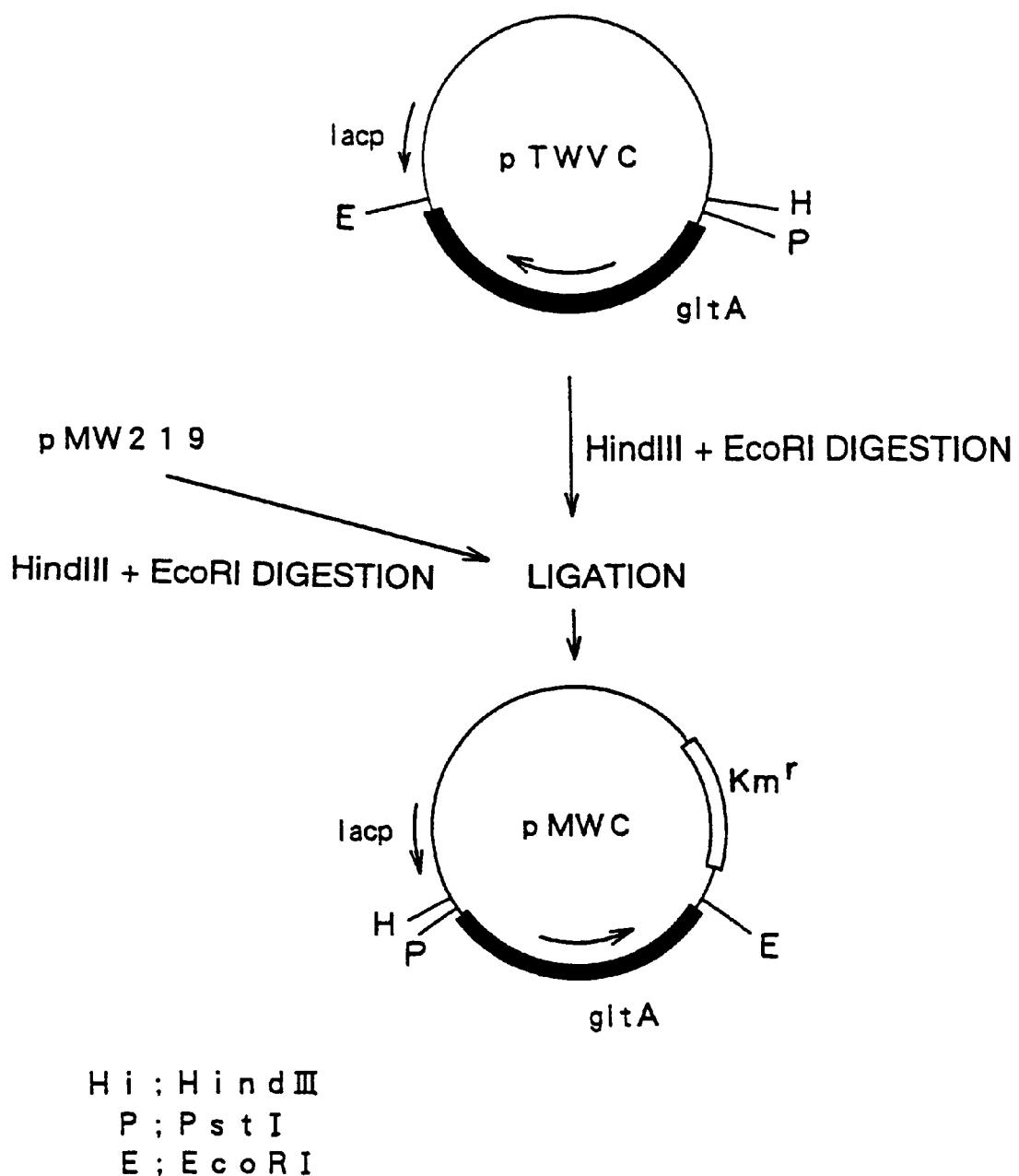
FIG. 3 shows construction of a plasmid pMWC having the gltA gene.

A DNA fragment having the gdhA gene obtained by digesting the pBRGDH with HindIII and SalI was purified and collected, and introduced into the HindIII-SalI site of a plasmid pMW219 (purchased from Nippon Gene) to obtain a plasmid pMWG (FIG. 2). Furthermore, a plasmid pTWVC having the gltA gene derived from *Escherichia coli* (WO97/08294) was digested with HindIII and EcoRI, and the resulting DNA fragment having the gltA gene was purified and collected, and introduced into the HindIII-EcoRI site of the plasmid pMW219 to obtain a plasmid pMWC (FIG. 3).

Figure 4:
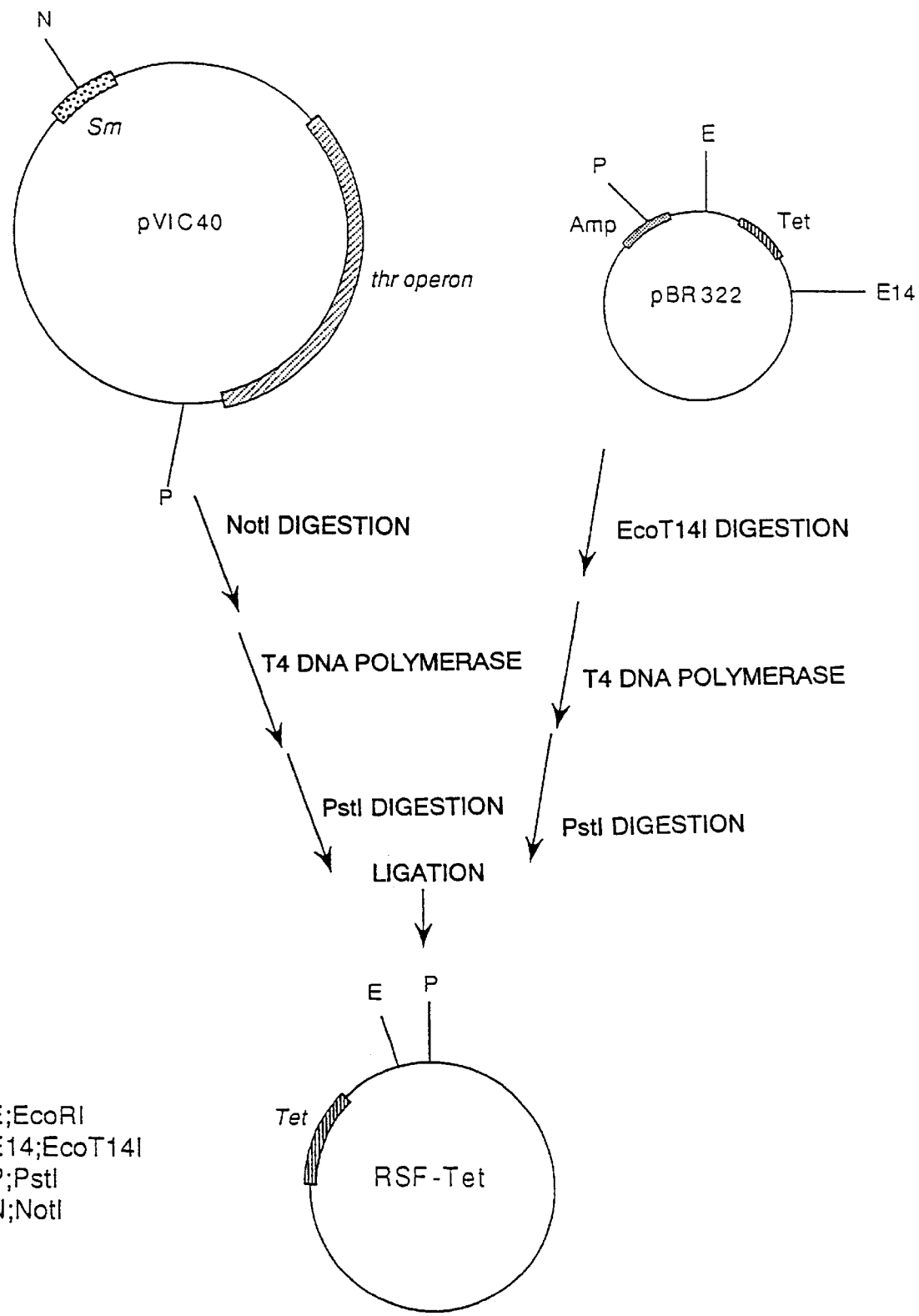
FIG. 4 shows construction of a plasmid RSF-Tet having a replication origin of a wide-host-range plasmid RSF1010 and a tetracycline resistance gene.

At the same time, a product obtained by digesting a plasmid pVIC40 having a replication origin of a wide-host-range plasmid RSF1010 (Japanese Patent Application Laid-Open (KOKAI) No. 8-047397(1996)) with NotI, followed by T4 DNA polymerase treatment and PstI digestion, and a product obtained by digesting pBR322 with EcoT14I, followed by T4 DNA polymerase treatment and PstI digestion, were mixed and ligated with T4 ligase to obtain a plasmid RSF-Tet having the replication origin of RSF1010 and a tetracycline resistance gene (FIG. 4).

Figure 5:
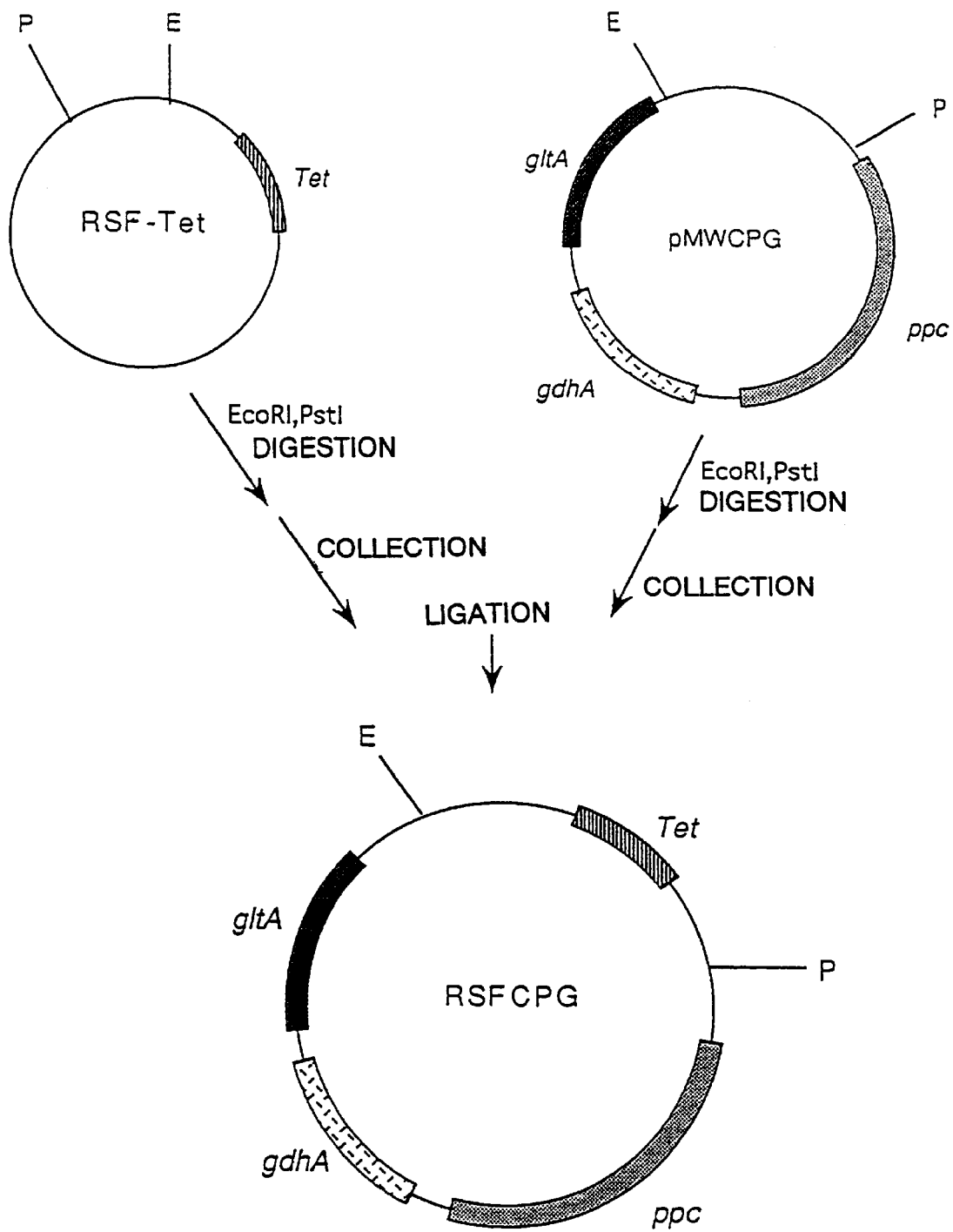
FIG. 5 shows construction of a plasmid RSFCPG having the replication origin of the wide-host-range plasmid RSF1010, the tetracycline resistance gene, the gltA gene, the ppc gene and the gdhA gene.

Then, the pMWCPG was digested with EcoRI and PstI, and a DNA fragment having the gltA gene, the ppc gene and the gdhA gene was purified and collected. Similarly, the RSF-Tet was digested with EcoRI and PstI, and a DNA fragment having the replication origin of RSF1010 was purified and collected. Those DNA fragments were mixed and ligated with T4 ligase to obtain a plasmid RSFCPG composed of RSF-Tet carrying the gltA gene, the ppc gene and the gdhA gene (FIG. 5). Expression of the gltA gene, the ppc gene and the gdhA gene by the resulting plasmid RSFCPG was confirmed based on complementation of auxotrophy of *Escherichia coli* strains lacking the gltA gene, the ppc gene or the gdhA gene, and measurement of each enzyme activity. Similarly, expression of the gdhA gene or the gltA gene by the pMWG or the pMWC was confirmed based on complementation of auxotrophy of *Escherichia coli* strains lacking the gdhA gene or the gltA gene, and measurement of each enzyme activity.

(2) Introduction of RSFCPG, pMWC and pMWG into Genus Klebsiella Bacterium and Genus Erwinia (Pantoea) bacterium and Evaluation of L-glutamic acid productivity The *Erwinia herbicola* IAM1595 (Pantoea agglomerans AJ2666) and *Klebsiella planticola* AJ13399 were transformed with the RSFCPG, pMWC and pMWG by electroporation (Miller J. H., "A Short Course in Bacterial Genetics; Handbook" Cold Spring Harbor Laboratory Press, USA, 1992) to obtain transformants exhibiting tetracycline resistance.

Each of the resulting transformants and the parent strains was inoculated into 50 ml-volume large size test tube containing 5 ml of a culture medium comprising 40 g/L glucose, 20 g/L ammonium sulfate, 0.5 g/L magnesium sulfate heptahydrate, 2 g/L potassium dihydrogenphosphate, 0.5 g/L sodium chloride, 0.25 g/L calcium chloride heptahydrate, 0.02 g/L ferrous sulfate heptahydrate, 0.02 g/L manganese sulfate tetrahydrate, 0.72 mg/L zinc sulfate dihydrate, 0.64 mg/L copper sulfate pentahydrate, 0.72 mg/L cobalt chloride hexahydrate, 0.4 mg/L boric acid, 1.2 mg/L sodium molybdate dihydrate, 2 g/L yeast extract, and 30 g/L calcium carbonate, and cultured at 37° C. with shaking until the glucose contained in the culture medium was consumed. To the culture medium of the transformants, 25 mg/L of tetracycline was added. After the cultivation was completed, L-glutamic acid accumulated in the culture medium was measured. The results are shown in Table 1.

TABLE 1

| Accumulated amount of L-glutamic acid | |
| --- | --- |
| Bacterial strain | Accumulated amount of L-glutamic acid |
| IAM1595 | 0.0 g/L |
| IAM1595/RSFCPG | 5.0 |
| AJ13399 | 0.0 |
| AJ13399/RSFCPG | 3.1 |
| AJ13399/pMWC | 2.5 |
| AJ13399/pMWG | 0.8 |
| Culture medium alone | 0.2 |

While the *Erwinia herbicola* IAM1595 and *Klebsiella planticola* AJ13399 did not accumulate L-glutamic acid, the strains whose CS, PEPC and GDH activities were amplified by introducing RSFCPG accumulated 5.0 g/L and 3.1 g/L of L-glutamic acid, respectively. The AJ13399 strain of which CS activity alone was amplified accumulated 2.5 g/L of L-glutamic acid, and the strain of which GDH activity alone was amplified also accumulated 0.8 g/L of L-glutamic acid.

(3) Cloning of Fragment having Part of αKGDH Gene of *Klebsiella Planticola* AJ13399

Cloning of a fragment having a part of the αKGDH gene of *Klebsiella planticola* AJ13399 was performed by PCR using oligonucleotides each having a nucleotide sequence of a homologous region of the αKGDH gene of the organisms whose nucleotide sequences had been already reported, i.e., *Azotobacter vinelandii*, *Bacillus subtilis*, *Escherichia coli*, *Corynebacterium glutamicum*, *Haemophilus influenzae*, human and *Saccharomyces cerevisae* (Eur. J. Biochem. Vol.

187, pp.235–239, 1990; Mol. Gen. Genet. Vol. 234, pp.285–296, 1992; Eur. J. Biochem. Vol. 141, pp.351–359, 1984; Microbiology, Vol. 142, pp.3347–3354, 1996; Science, Vol. 269, pp.496–512, 1995; Proc. Natl. Acad. Sci. U.S.A. Vol. 89, pp.1963–1967, 1992; and Mol. Cel. Biol. Vol. 9, pp.2695–2705, 1989), and an EcoRI site as primers.

Specifically, the followings are used as the primers.
(Primer 1)
5' CCGGGAATTCGGTGACGTNAARTAYCA 3' (SEQ ID NO: 1)
(Primer 2)
5' GGCGAATTCGGGAACGGGTASAGYTGYTC 3' (SEQ ID NO: 2)

The chromosome DNA of the *Klebsiella planticola* AJ13399 used as a template of PCR was isolated by the same method as conventionally used for extracting chromosome DNA from *Escherichia coli* (Seibutsu Kogaku Jikkensho (Textbook of Bioengineering Experiments), Ed. by the Society of Fermentation and Bioengineering, Japan, p. 97–98, Baifukan, 1992).

The PCR was performed with a cycle consisting of 94° C. for 1 minute, 50° C. for 1 minute, and 73° C. for 3 minutes, which was repeated for 30 cycles, and the resulting DNA fragment was digested with EcoRI, and inserted into a vector plasmid pT7Blue digested with EcoRI to obtain a recombinant plasmid pT7KP. The vector plasmid pT7Blue (ampicillin resistant) used was a commercial product from Novagen.

The DNA nucleotide sequence of the cloned fragment and the amino acid sequence encoded by the sequence are shown in SEQ ID NO: 3. The same amino acid sequence is solely represented in SEQ ID NO: 4. The sequence showed 82.3% of homology to the αKGDH-E1 subunit gene of *Escherichia coli* (hereinafter referred to as "SUCA gene"), and it is clearly recognized as a part of the sucA gene of *Klebsiella planticola* AJ13399. In the nucleotide sequence shown in SEQ ID NO: 3, the nucleotide numbers 18–1659 are derived from the sucA gene, and the nucleotide numbers 0–17 and 1660–1679 are derived from the primers.

(4) Acquisition of Strain Deficient in αKGDH Derived from *Klebsiella planticola* AJ13399

A strain of *Klebsiella planticola* deficient in αKGDH was obtained by homologous recombination using the fragment having a part of the sucA gene of *Klebsiella planticola* obtained as described above.

First, pT7KP was digested with BstEII and, to this cleaved site, a kanamycin resistance gene fragment, which had been cloned by PCR from a plasmid pNEO (purchased from Pharmacia) and into both ends of which BstEII sites were introduced, was introduced to obtain a plasmid pT7KPKm, in which the kanamycin resistance gene was inserted into the central part of the sucA gene of *Klebsiella planticola*.

The primers used for the cloning of the kanamycin resistance gene were as follows.
(Primer 3)
5' TACTGGGTCACCTGACAGCTTATCATCGAT 3' (SEQ ID NO: 5)
(Primer 4)
5' CGTTCGGTGACCACCAAAGCGGCCATCGTG 3' (SEQ ID NO: 6)

Then, the PT7KPKm was cleaved with KpnI and, to this cleaved site, a tetracycline resistance gene fragment, which had been cloned by PCR from a plasmid pBR322 (purchased from Takara Shuzo) and into both ends of which KpnI sites were introduced, was introduced to obtain a plasmid pT7KPKmTc, in which the kanamycin resistance gene was inserted into the central part of the sucA gene of *Klebsiella planticola* together with the inserted flanking tetracycline resistance gene.

The primers used for the cloning of the tetracycline resistance gene were as follows.
(Primer 5)
5' GGGGTACCCAAATAGGCGTATCACGAG 3' (SEQ ID NO: 7)
(Primer 6)
5' GGGGTACCCGCGATGGATATGTTCTG 3' (SEQ ID NO: 8)

Subsequently, the plasmid pT7KPKmTc was digested with SacI and XbaI to cut out a DNA fragment having the kanamycin resistance gene inserted into the central part of the sucA gene of *Klebsiella planticola* together with the inserted flanking tetracycline resistance gene, and this was inserted into a gram-negative bacterium chromosome-inserted plasmid vector pGP704 (Marta Herrero et al., Journal of Bacteriology, 1990, 172, p.6557–6567) digested with SacI and XbaI to obtain a plasmid pUTONOTK.

Using the plasmid pUTONOTK obtained as described above, *Klebsiella planticola* AJ13399 was transformed by electroporation, and a strain in which the plasmid pUTONOTK was inserted into the chromosome by homogenous recombination of the sucA gene fragment was selected based on the tetracycline resistance and the kanamycin resistance. From this strain, a *Klebsiella planticola* AJ13410 strain lacking the sucA, in which the sucA gene on the chromosome was replaced with the sucA gene into which the kanamycin resistance gene was inserted at the central part, was further obtained based on the tetracycline sensitivity and the kanamycin resistance.

To confirm that the AJ13410 strain obtained as described above was deficient in the αKGDH activity, its enzymatic activity was determined by the method of Reed (L. J. Reed and B. B. Mukherjee, Methods in Enzymology 1969, 13, p.55–61). As a result, the αKGDH activity could not be detected in the AJ13410 strain as shown in Table 2, and thus it was confirmed that the strain lacked the sucA as desired.

TABLE 2

| Bacterial strain | αKGDH activity (ΔABS/min/mg protein) |
|---|---|
| AJ13399 | 0.101 |
| AJ13410 | <0.002 |

(5) Evaluation of L-glutamic Acid Productivity of *Klebsiella Planticola* Strain Deficient in αKGDH Each of the AJ13399 and AJ13410 strains was inoculated into a 500 ml-volume flask containing 20 ml of a culture medium comprising 40 g/L glucose, 20 g/L ammonium sulfate, 0.5 g/L magnesium sulfate heptahydrate, 2 g/L potassium dihydrogenphosphate, 0.5 g/L sodium chloride, 0.25 g/L calcium chloride heptahydrate, 0.02 g/L ferrous sulfate heptahydrate, 0.02 g/L manganese sulfate tetrahydrate, 0.72 mg/L zinc sulfate dihydrate, 0.64 mg/L copper sulfate pentahydrate, 0.72 mg/L cobalt chloride hexahydrate, 0.4 mg/L boric acid, 1.2 mg/L sodium molybdate dihydrate, 2 g/L yeast extract, 30 g/L calcium carbonate, 200 mg/L L-lysine monohydrochloride, 200 mg/L L-methionine, and DL-α,ε-diaminopimelic acid (DAP), and cultured at 37° C. with shaking until the glucose contained in the culture medium was consumed. After the cultivation was completed, L-glutamic acid and α-ketoglutaric acid (abbreviated as "αKG" hereinafter)

accumulated in the culture medium were measured. The results are shown in Table 3.

TABLE 3

Accumulated amounts of L-glutamic acid and αKG

| Bacterial strain | Accumulated amount of L-glutamic acid | Accumulated amount of αKG |
|---|---|---|
| AJ13399 | 0.0 g/L | 0.0 g/L |
| AJ13410 | 12.8 | 1.5 |

The AJ13410 strain deficient in the αKGDH activity accumulated 12.8 g/L of L-glutamic acid, and simultaneously accumulated 1.5 g/L of αKG.

(6) Introduction of RSFCPG into *Klebsiella Planticola* Strain Deficient in αKGDH and Evaluation of L-glutamic Acid Productivity The AJ13410 strain was transformed with the RSFCPG, and the resulting RSFCPG-introduced strain, AJ13410/RSFCPG, was inoculated into a 500 ml-volume flask containing 20 ml of a culture medium comprising 40 g/L glucose, 20 g/L ammonium sulfate, 0.5 g/L magnesium sulfate heptahydrate, 2 g/L potassium dihydrogenphosphate, 0.5 g/L sodium chloride, 0.25 g/L calcium chloride heptahydrate, 0.02 g/L ferrous sulfate heptahydrate, 0.02 g/L manganese sulfate tetrahydrate, 0.72 mg/L zinc sulfate dihydrate, 0.64 mg/L copper sulfate pentahydrate, 0.72 mg/L cobalt chloride hexahydrate, 0.4 mg/L boric acid, 1.2 mg/L sodium molybdate dihydrate, 2 g/L yeast extract, 25 mg/L tetracycline, 30 g/L calcium carbonate, 200 mg/L L-lysine monohydrochloride, 200 mg/L L-methionine, and DL-α,ε-DAP, and cultured at 37° C. with shaking until the glucose contained in the culture medium was consumed. After the cultivation was completed, L-glutamic acid and αKG accumulated in the culture medium were measured. The results are shown in Table 4.

TABLE 4

Accumulated amounts of L-glutamic acid and αKG

| Bacterial strain | Accumulated amount of L-glutamic acid | Accumulated amount of αKG |
|---|---|---|
| AJ13410 | 12.8 g/L | 1.5 g/L |
| AJ13410/RSFCPG | 24.2 | 0.0 |

In the strain of which CS, PEPC and GDH activities were amplified by the introduction of RSFCPG, the accumulated amount of αKG was reduced, and the accumulated amount of L-glutamic acid was further improved.

What is claimed is:

1. A biologically pure culture of a microorganism belonging to the genus Erwinia or the genus Pantoea and having an ability to produce L-glutamic acid extracellularly, said microorganim having been modified so that the microorganism has an increased activity of an enzyme catalyzing a reaction for L-glutamic acid biosynthesis.

2. The biologically pure culture of a microorganism according to claim 1 which is Pantoea agglomerans.

3. The biologically pure culture of a microorganism according to claim 1 which has been modified so that the microorganism has an increased activity of at least one selected from the group consisting of citrate synthase, phosphoenolpyruvate carboxylase, and glutamate dehydrogenase.

4. The biologically pure culture of a microorganims according to claim 3 which has been modified so that the microorganism has increased activities of citrate synthase, phosphoenolpyruvate carboxylase, and glutamate dehydrogenase.

5. The biologically pure culture of a microorganims according to claim 1 which has been modified so that the microorganim has a decreased activity of, or is deficient in an activity of at least one enzyme selected from the group consisting of α-ketoglutarate dehydrogenase, isocitrate lyase, phosphate acetyltransferase, acetate kinase, acetohydroxy acid synthase, acetolactate synthase, formate acetyltransferase, lactate dehydrogenase, L-glutamate decarboxylase, and 1-pyrroline dehydrogenase.

6. The biologically pure culture of a microorganism according to claim 5 which has been modified so that the microorganism has a decreased activity of, or is deficient in an activity of α-ketoglutarate dehydrogenase.

7. The biologically pure culture of a microorganism according to claim 3 which has been modified so that the microorganism has a decreased activity of, or is deficient in an activity of at least one enzyme selected from the group consisting of α-ketoglutarate dehydrogenase, isocitrate lyase, phosphate acetyltransferase, acetate kinase, acetohydroxy acid synthase, acetolactate synthase, formate acetyltransferase, lactate dehydrogenase, L-glutamate decarboxylase, and 1-pyrroline dehydrogenase.

8. The biologically pure culture of a microorganism according to claim 4 which has been modified so that the microorganism has a decreased activity of, or is deficient in an activity of at least one enzyme selected from the group consisting of α-ketoglutarate dehydrogenase, isocitrate lyase, phosphate acetyltransferase, acetate kinase, acetohydroxy acid synthase, acetolactate synthase, formate acetyltransferase, lactate dehydrogenase, L-glutamate decarboxylase, and 1-pyrroline dehydrogenase.

9. A biologically pure culture of a microorganism belonging to the genus Kiebsiella and having an ability to produce L-glutamic acid extracelluarly, said microorganism having been modified (1) so that the microorganism has an increased activity of an enzyme catalyzing a reaction for L-glutamic acid biosynthesis and (2) so that the microorganism has a decreased activity of, or is deficient in an activity of at least one enzyme selected from the group consisting of α-ketoglutarate dehydrogenase, isocitrate lyase, phosphate acetyltransferase, acetate kinase, acetohydroxy acid synthase, acetolactate synthase, formate acetyltransferase, lactate dehydrogenase, L-glutamate decarboxylase, and 1-pyrroline dehydrogenase.

10. The biologically pure culture of a microorganism according to claim 9 which is *Kiebsiella planticola.*

11. The biologically pure culture of a microorganism according to claim 9, which has been modified so that the microorganism has an increased activity of at least one selected from the group consisting of citrate synthase, phoshoenolpyruvate carboxylase, and glutamate dehydrogenase.

12. The biologically pure culture of a microorganism according to claim ,11 which has been modified so that the microorganism has an increased activity of at least one selected from the group consisting of citrate synthase, phoshoenolpyruvate carboxylase, and glutamate dehydrogenase.

13. The biologically pure culture of a microorganism according to claim 9 which has been modified so that the microorganism has a decreased activity of, or is deficient in an activity of α-ketoglutarate dehydrogenase.

* * * * *

UNITED STATES PATENT AND TRADEMARK OFFICE
CERTIFICATE OF CORRECTION

PATENT NO. : 6,682,912 B2
DATED : January 27, 2004
INVENTOR(S) : Mika Moriya et al.

It is certified that error appears in the above-identified patent and that said Letters Patent is hereby corrected as shown below:

Column 23,
Line 3, "Erwinia" should read -- *Erwinia* --; and "Pantoea" should read -- *Pantoea* --;
Line 5, "microorganim" first occurrence, should read -- microorganism --;
Line 9, "Pantoea agglimerans" should read -- *Pantoes agglimerans* --;
Lines 16 and 21, "microorganims" should read -- microorganism --.

Column 24,
Line 11, "Kiebsiella" should read -- *Klebsiella* --;
Line 24, "Kiebsiella planticola" should read -- *Klebsiella planticola* --;
Lines 29 and 35, "phoshoenolpyruvate" should read -- *phosphoenolpyruvate* --;
Line 32, "claim, 11" should read -- claim 11 --.

Signed and Sealed this

Twenty-ninth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO.     : 6,682,912 B2
DATED          : January 27, 2004
INVENTOR(S)    : Mika Moriya et al.

It is certified that error appears in the above-identified patent and that said Letters Patent is hereby corrected as shown below:

Column 23,
Line 3, "Erwinia" should read -- *Erwinia* --; and "Pantoea" should read -- *Pantoea* --;
Line 5, "microorganim" first occurrence, should read -- microorganism --;
Line 9, "Pantoea agglimerans" should read -- *Pantoe agglomerans* --;
Lines 16 and 21, "microorganims" should read -- microorganism --.

Column 24,
Line 11, "Kiebsiella" should read -- *Klebsiella* --;
Line 24, "Kiebsiella planticola" should read -- *Klebsiella planticola* --;
Lines 29 and 35, "phoshoenolpyruvate" should read -- *phosphoenolpyruvate* --;
Line 32, "claim, 11" should read -- claim 11 --.

This certificate supersedes Certificate of Correction issed June 29, 2004.

Signed and Sealed this

Third Day of August, 2004

JON W. DUDAS
*Acting Director of the United States Patent and Trademark Office*